United States Patent [19]

Prindle

[11] Patent Number: 4,715,853
[45] Date of Patent: Dec. 29, 1987

[54] BACK-FILL SYRINGE

[75] Inventor: Gordon E. Prindle, Schaumberg, Ill.

[73] Assignee: Ideal Instruments, Inc., Chicago, Ill.

[21] Appl. No.: 909,481

[22] Filed: Sep. 19, 1986

[51] Int. Cl.[4] .............................................. A61M 5/18
[52] U.S. Cl. .................................. 604/184; 604/247; 604/257
[58] Field of Search ............... 604/184, 183, 181, 247, 604/255, 256, 257, 403, 407, 411

[56] References Cited

U.S. PATENT DOCUMENTS

| | | | |
|---|---|---|---|
| 1,995,971 | 3/1935 | Dowling. | |
| 2,374,368 | 4/1945 | Mejia. | |
| 2,645,224 | 7/1953 | Beebe | 604/183 |
| 2,757,670 | 8/1956 | Ogle | 604/407 |
| 2,821,193 | 1/1958 | Ziherl et al. | 604/184 X |
| 2,821,195 | 1/1958 | McLintock | 604/184 |
| 2,851,201 | 9/1958 | Poitras et al. | 604/407 X |
| 3,353,537 | 11/1967 | Knox et al. | |
| 3,400,716 | 9/1968 | Schultz | 604/184 |
| 4,204,539 | 5/1980 | Van Brugge. | |
| 4,261,359 | 4/1981 | Chein | 604/184 |
| 4,530,695 | 7/1985 | Phillips et al. | 604/184 |

FOREIGN PATENT DOCUMENTS 933101 7/1982 U.S.S.R. .

Primary Examiner—John D. Yasko
Attorney, Agent, or Firm—Ian C. McLeod

[57] ABSTRACT

A back fill syringe assembly (10) which is supplied by a fluid from a bottle (12) through a tube (11) is described. The syringe assembly preferably automatically refills upon injection of an animal.

16 Claims, 5 Drawing Figures

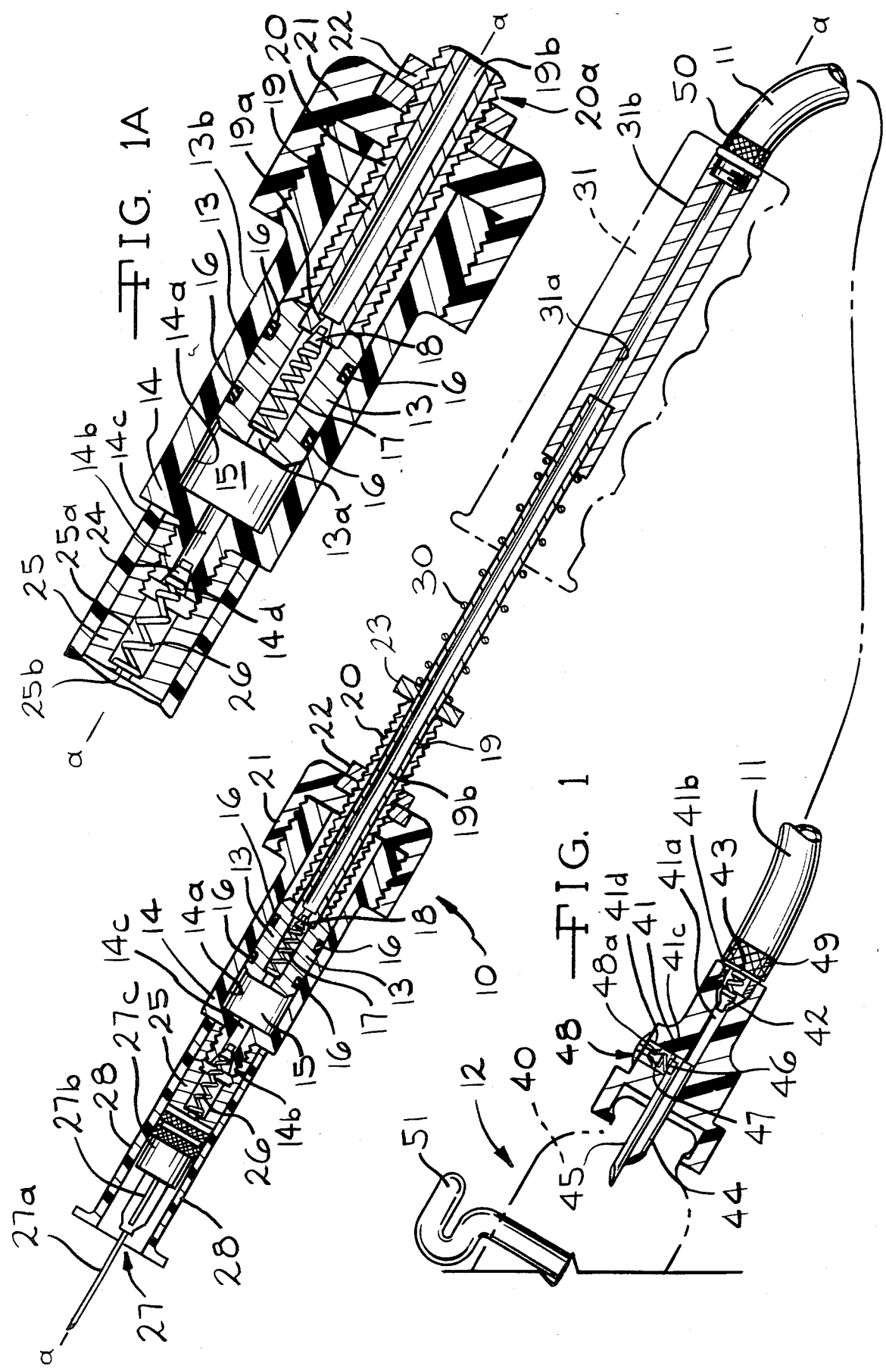

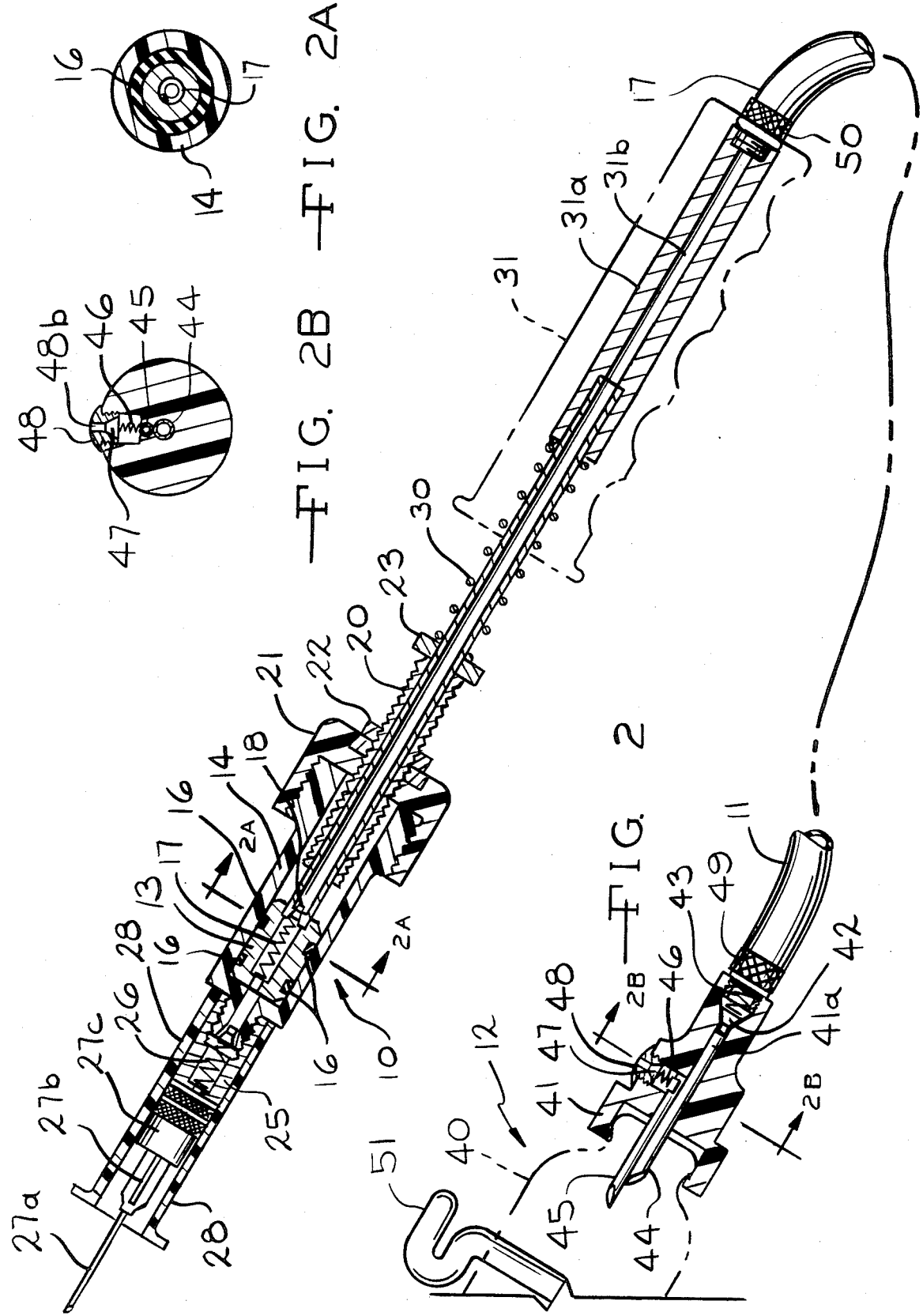

BACK-FILL SYRINGE

BACKGROUND OF THE INVENTION (1) Summary of the Invention

The present invention relates to a syringe which on the plunging stroke of a piston injects a liquid through a needle into an animal and which refills with the liquid upon retraction of the piston. In particular, the present invention relates to a syringe which is filled from behind at an end opposite the needle from a bottle which is connected by a tube to the back of the syringe, thereby the name "back-fill syringe".

(2) Prior Art

U.S. Pat. No. 2,374,368 to Mejia discloses a valved syringe with an open supply reservoir. U.S. Pat. No. 1,995,971 to Dowling and U.S. Pat. No. 3,353,537 to Knox et al describe two valve syringes. U.S. Pat. No. 4,204,539 to Brugge discloses a hand operated apparatus with two valves. None of these patents describe a "stick" syringe with automatic refilling of the syringe from a refill bottle which is valved to allow only air inlet so that the device can be used under "field" conditions with large animals such as cattle. Where the bottle is open, the bottle can not be carried on the person of the operator.

Another syringe apparatus is described in Russian Patent No. 933,101 to Timoshin. This patent describes a single-hand operation veterinary instrument for injecting livestock which incorporates systems for automatic sterilization of the injection needle and for disinfection and marking of the injected area with a colored disinfectant solution. A syringe, injection needle holder and ejector, and a bellows operated pump are mounted on a pistol-type grip body. The inlet of the syringe is connected by plastic tubing and a two-way valve to a bottle of veterinary preparation. The outlet is connected by plastic tubing and a sleeve to the injection needle. The inlet of the bellows is connected by plastic tubing to a bottle of colored disinfectant solution. The outlet is connected by plastic tubing and a sleeve to a spray on the injection needle holder. The ejector comprises a spring loaded striker which is activated by a trigger lever, the length of travel being controlled by stops. This device is complicated and has external hoses across the pistol grip body of the syringe which can easily become detached or damaged.

OBJECTS

It is therefore an object of the present invention to provide a back-fill syringe which has few moving parts and no exposed hoses across the body of the syringe and which is closed except for air inlet into a bottle holding the fluid to be dispensed and fluid outlet from the needle and which can be used under "field" conditions mounted on the operator. Further it is an object of the present invention to provide an apparatus which is reliable and relatively simple and inexpensive to construct. These and other objects will become increasingly apparent by reference to the following description and the drawings.

IN THE DRAWINGS

FIG. 1 is a front cross-sectional view illustrating a back-fill syringe 10 and a bottle 12 connected by a tube 11 wherein the liquid is to be dispensed from chamber 15 by means of piston 13.

FIG. 1A is an enlarged partial sectional view of FIG. 1 showing the valve bodies 18 and 24 which control fluid flow through the piston 13.

FIG. 2 is a front cross-sectional view of the syringe 11 and bottle 12 shown in FIG. 1 wherein the piston 13 has dispensed the fluid through the needle 27.

FIG. 2A is an end cross-sectional view along lines 2A—2A of FIG. 2 particularly showing the preferred circular cross-section of the piston 13.

FIG. 2B is an end cross-sectional view along line 2B—2B of FIG. 2 particularly showing the vented plug 48.

GENERAL DESCRIPTION

The present invention relates to a syringe assembly and dispensing bottle assembly which reloads a liquid to be dispensed by the syringe assembly after injecting a dose of the liquid into an animal which comprises: a piston means movable along a longitudinal axis for dispensing the liquid from the syringe assembly and which has an opening along the axis; a sleeve means confining the piston means for movement along the longitudinal axis and defining a chamber with the piston means for holding the liquid prior to dispensing, the sleeve means having a dispensing end with an opening for discharging the liquid through a needle means mounted on the dispensing end and a charging end for receiving the liquid; tubular means connected at one end to the piston means along the longitudinal axis and extending from the charging end of the sleeve means to provide movement of the piston means in the cylinder and to provide fluid connection to the opening in the piston means; handle means mounted on the tubular means away from the charging end of the sleeve means such that the tubular means can be moved to push the piston in the sleeve means by hand; hose means connected to the tubular means at an end opposite the one end of the tubular means; bottle means connected to the hose means; one-way valve means in the dispensing end of the sleeve means, in the opening in the piston means and in the bottle, whereby the liquid can be dispensed from the chamber through the dispensing end of the sleeve means and needle assembly by the piston means with the valve means in the dispensing end open and with the valve means in the tubular member or piston means and the bottle closed and whereby the chamber is refilled from the bottle by closing the valve means in the dispensing end and by opening the valve means in the piston means and in the bottle; and additional one-way valve means for air inlet into the bottle means which allows air to enter the bottle means as the chamber in the sleeve means is refilled. The syringe assembly is particularly adapted to being carried on the person of the operator.

Further the present invention relates to a method for dispensing a liquid from a syringe assembly and dispensing bottle assembly which reloads a liquid to be dispensed by the syringe assembly after injecting a dose of the liquid into an animal which comprises: providing the syringe assembly which comprises a piston means movable along a longitudinal axis for dispensing the liquid from the syringe assembly and which has an opening along the axis; a sleeve means confining the piston means for movement along the longitudinal axis and defining a chamber with the piston means for holding the liquid prior to dispensing, the sleeve means having a dispensing end with an opening for discharging the liquid through a needle means mounted on the dispensing end and a charging end for receiving the liquid; tubular means connected at one end to the piston means along the longitudinal axis and extending from the charging end of the sleeve means to provide movement of the piston in the cylinder and to provide fluid connection to the opening in the piston means; handle means mounted on the tubular means away from the charging end of the sleeve means such that the tubular means can be moved to push the piston means in the sleeve means by hand; hose means connected to the tubular means at an end opposite the one end of the tubular means; bottle means connected to the hose means; one-way valve means in the dispensing end of the sleeve means, the opening in the piston means and in the bottle means, whereby the liquid can be dispensed from the chamber through the dispensing end of the sleeve means and needle assembly by the piston means with the valve means in the dispensing end open and with the valve means in the tubular means or piston means and the bottle closed and whereby the chamber is refilled from the bottle by closing the valve means in the dispensing end and by opening the valve means in the piston means and in the bottle and additional one-way valve means for air inlet into the bottle means which allows air to enter the bottle means as the chamber in the sleeve means is refilled; and dispensing the liquid by pushing the syringe assembly against the animal; and retracting the piston means in the sleeve means to refill the chamber.

SPECIFIC DESCRIPTION

FIGS. 1, 1A and 2 show the back-fill syringe assembly 10 of the present invention connected by a flexible hose 11 to a bottle assembly 12. The syringe assembly 10 includes a piston 13 mounted around longitudinal axis a—a of a cylindrical wall 14a in a sleeve or housing 14. As shown in FIGS. 1 and 1A a chamber 15 is defined by the piston 13 and the housing 14. O-rings 16 are provided around the piston 13 and engage the cylindrical wall 14a of the housing 14. The piston 13 is provided with a hollow bore 13a around the longitudinal axis a—a which has an enlarged portion 13b supporting a spring 17 extending away from the chamber 15. The spring 17 engages a conically shaped one-way valve body 18 and urges the valve body 18 into a conically shaped recess 19a in tubular member 19 mounted on the piston 13 along the axis a—a. The tubular member 19 is slideably mounted in a journal member 20 mounted through cover 21 on housing 14 and extends away from the housing 14. The tubular member 19 has a bore 19b throughout its length along axis a—a. The cover 21 threads onto the housing 14. The journal member 20 is provided with external threads 20a which engage a knurled nut 22 which locks the journal member 20 in position on cover 21 after the journal member 20 is positioned in cover 21. A knurled knob 23 is mounted on the sleeve 20 to allow hand adjustment of the journal member 20 in the cover 21 to move the piston 13 further into or out of the bore 13a to thereby change the size of the chamber 15. A small discharge conduit 14b with an opening 14c from the housing 14 is provided along axis a—a leading to a one-way conically shaped one way tapered valve body 24 lodged in a tapered seat 14d in the opening 14c. A holder 25 is mounted on the conduit 14b supporting coil spring 26 in a recess 25a with a second discharge opening 25b leading to a conventional needle 27 assembly including a hub 27b and needle 27a extending from a conventional luer lock 27c. A shield 28 is provided around the needle assembly 27, luer lock 27c and holder 25 to limit the penetration of the needle 27a into an animal. A coil spring 30 is provided around the outside of the tubular member 19 with one end engaging the second nut 23 and with the other end engaging a handle 31 with a conduit 31a with opening 31b along axis a—a secured inside.

Thus as can be seen from FIGS. 1, 1A, 2, 2A and 2B, the shield 28 engages the animal with the needle 27a in the flesh. The handle 31 is pushed to dispense the liquid from chamber 15 through valve body 24 which is opened by the movement of the liquid to force the liquid through the seat 14d. The valve body 18 is closed on seat 19a by the force of the liquid during the dispensing of the liquid from the needle 27a as shown in FIG. 2. Upon release of the dispensing force from the handle 31, the coil spring 30 automatically pushes the piston 13 back in the housing 14 so that the chamber 15 is reformed during which the valve body 24 is seated and the valve body 18 is opened to allow liquid to flow into the chamber 15 from the bottle 12 through hose 11 as shown in FIG. 1. This cycle is repeated each time an animal is injected.

FIGS. 1, 2 and 2B show the details of the bottle assembly 12 including bottle 40 with cap 41 locked onto bottle 40. The cap 41 has a central bore 41a having a conical valve seat 41b for a conically shaped one way valve body 42 urged by spring 43 into the seat 41b. The bore 41a supports a fluid conduit 44 which is immersed in the liquid in the bottle 40 in use. A second conduit 45 is supported in a second bore 41c in cap 41. A third bore 41a is provided in the cap 41 perpendicular to the second bore 41c and supporting a spring 46 engaging a conically shaped one way valve body 47. A valve seat 48a is provided in vented plug 48 which has an opening 48b outside of the bottle 40. Conventional threaded connectors 49 and 50 are provided at the ends of flexible hose 11 to connect to conduit 31a in handle 31 and to cap 41. A clip 51 or other holder means can be provided on bottle 40 to hold the bottle on a belt or the like.

As can be seen from FIGS. 1 and 2, the liquid in bottle 40 is fed through hose 11 as the piston 13 is retracted from the position shown in FIG. 2. The valve body 42 unseats from the seat 41b to allow liquid to flow from the bottle 40 and the valve body 47 unseats from seat 41d to allow air to enter the bottle to replace the liquid which is dispensed by the syringe assembly 10.

The position of the valve bodies 18, 24, 42 and 47 in dispensing and filling from the chamber 15 is as follows in Table I:

TABLE I

| Dispensing from Chamber 15 | |
|---|---|
| Valve body | Open or Closed |
| 18 | closed |
| 24 | open |
| 42 | closed |
| 47 | closed |
| Filling Chamber 15 | |
| 24 | closed |
| 18 | open |
| 42 | open |
| 47 | open |

As can be seen from the foregoing description the one-way valve bodies 18, 24, 42 and 48 are preferably conical as are the corresponding seats 14d, 19a, 41b and 48a. Most preferably the valve bodies 18, 24, 42 and 48 are made of rubber to insure a complete seal. Other types of one-way valve means such as balls which engage semi-circular seats can be used as is well known to those skilled in the art. Preferably coil spring means such as springs 17, 26, 43 and 47 are used to urge the valve bodies 18, 24 and 48 into the seats 14d, 19a, 41b and 48a since this allows liquid to pass through the spring and allows ease of disassembly and cleaning.

Preferably the piston 13 and housing 14 are cylindrical in cross-section as shown in FIGS. 1, 1A and 2. This allows ease of construction of the syringe assembly 10. The housing 14 and cap 21 can be constructed of clear plastic to allow visual inspection of the chamber 15 and the inside of the syringe assembly 10.

Preferably spring 30 is used to retract the piston 13 in the housing 14 to refill the chamber 15. It will be appreciated that this can be done manually. Also, preferably the syringe chamber 15 has a volume of 1 cc or 5 cc.

Numerous variations will occur to those skilled in the art. It is intended that the foregoing description be only illustrative of the present invention and that this invention be limited only to the hereinafter appended claims.

I claim:

1. A syringe assembly and dispensing bottle means which reloads a liquid to be dispensed by the syringe assembly after injecting a dose of the liquid into an animal which comprises:
   (a) a piston means movable along a longitudinal axis for dispensing the liquid from the syringe assembly and which has an opening along the axis;
   (b) a sleeve means confining the piston means for movement along the longitudinal axis and defining a chamber with the piston means for holding the liquid prior to dispensing, the sleeve means having a dispensing end with an opening for discharging the liquid through a needle means mounted on the dispensing end and a charging end for receiving the liquid;
   (c) tubular means connected at one end to the piston means along the longitudinal axis and extending from the charging end of the sleeve means to provide movement of the piston means in the sleeve means and to provide a fluid connection from the dispensing bottle means to the opening in the piston means;
   (d) handle means grippable by one hand mounted on the tubular means away from the charging end of the sleeve means such that the tubular means can be moved to push the piston means in the sleeve means along the longitudinal axis by the hand on the handle means;
   (e) hose means connected to the tubular means at an end opposite the one end of the tubular means;
   (f) bottle means connected to the hose means;
   (g) one-way valve means in the dispensing end of the sleeve means, the opening in the piston means or in the tubular means and in the bottle means, whereby the liquid can be dispensed from the chamber through the dispensing end of the sleeve means and needle means by the piston means with the valve means in the dispensing end open and with the valve means in the tubular means or piston means and the bottle means closed when the needle means is inserted into the animal and the fluid injected by pushing the handle means along the longitudinal axis and whereby the chamber is refilled from the bottle means by closing the valve means in the dispensing end and by opening the valve means in the piston means and in the bottle;
   (h) return means mounted on the assembly so as to move the piston means in the sleeve means back to the position for holding the liquid prior to dispensing and thus to refill the chamber; and
   (i) additional one-way valve means for air inlet into the bottle means which allows air to enter the bottle means as the chamber in the sleeve means is refilled by movement of the piston means in the sleeve means back to the position for holding the liquid prior to dispensing.

2. The syringe assembly of claim 1 wherein a coil spring means is provided as the return means around the tubular means between the sleeve means and the handle means to automatically retract the piston means in the sleeve means after the liquid is dispensesd from the chamber.

3. The syringe assembly of claim 1 wherein a shield means is provided around the needle means on the dispensing end of the sleeve means with a portion of the needle means projecting along the axis outside the shield means so that the depth of penetration of the needle means into the animal is limited by the shield means.

4. The syringe assembly of claim 1 wherein each of the one-way valve means has a conical seat and a valve body which is conical and wherein each valve body is urged into a resting closed position by a valve coil spring which engages the valve body.

5. The syringe assembly of claim 1 wherein the valve means in the piston means and in the discharge end of the sleeve means each includes a valve coil spring urging a conically shaped valve body into a conical seat and wherein a cap on the bottle means attached to the hose means supports one of the one way valve means with a valve coil spring urging a conical valve body into a conical valve seat in the cap.

6. The syringe assembly of claim 1 wherein the tubular means slides in an adjustable threaded journal member mounted threadably on the sleeve means with a threaded nut on the journal member which abuts on the sleeve means to lock the journal member in position, wherein the journal member limits movement of the piston means in the sleeve means when the chamber is refilled to thereby restrict the amount of fluid to be dispensed from the chamber.

7. The syringe assembly of claim 1 wherein the sleeve means comprises a cylindrical housing supporting the piston means and a cover over the housing with a threaded opening supporting a threaded journal member mounting the tubular means which engages the piston means prior to dispensing the liquid and movable into and out of the housing to change the size of the chamber by limiting the movement of the piston means in the housing when the chamber is refilled and wherein a threaded nut is provided on the journal member which locks the threaded journal member in position by engaging the the cap and wherein an adjusting knob is provided at an end of the journal member on an outside portion of the sleeve means for adjusting the position of the journal member in the cover.

8. the syringe assembly of claim 1 wherein the additional valve means means for air inlet into the bottle is mounted on a cap for the bottle, wherein a conduit containing one of the one-way valve means is provided in the cap for liquid inlet into the hose means and such that in use the bottle is inverted with the cap at a low point to supply liquid to the hose means and wherein the cap supports the one way valve means for the bottle and the additional valve means.

9. The syringe assembly of claim 1 wherein the bottle means is provided with a holder means for hanging the bottle means on an operator during dispensing of the liquid into the animal.

10. A method for dispensing a liquid from a syringe assembly and dispensing bottle means which reloads a liquid to be dispensed by the syringe assembly after injecting a dose of the liquid into an animal which comprises:

(a) providing the syringe assembly which comprises: a piston means movable along a longitudinal axis for dispensing the liquid from the syringe assembly and which has an opening along the axis; a sleeve means confining the piston for movement along the longitudinal axis and defining a chamber with the piston means for holding the liquid prior to dispensing, the sleeve means having a dispensing end with an opening for discharging the liquid througha needle means mounted on the dispensing end and a charging end for receiving the liquid; tubular menas connected at one end to the piston means along the lingitudinal axis and extending from the charging end of the sleeve means to provide movement of the piston means in the sleeve means and to provide fluid connection to the opening in the piston means; handle means grippable by one hand mounted on the tubular means away from the charging end of the sleeve means such that the tubular means can be moved to push the piston means in the sleeve means along the longitudinal axis by the hand on the handle means; hose means connected to the tubular menas at an end opposite the one end of the tubular means; bottle means connected to the hose means; one-way valve means in the dispensing end of the sleeve means, the opening in the piston means on the tubular means and in the bottle, wherby the liquid can be dispensed from the chamber through the dispensing end of the sleeve means and needle means by the piston means with the valve means in the dispensing end open and with the valve means in the tubular means or piston means and the bottle means closed when the needle means is inserted into the animal and fluid injected by pushing the handle means along the longitudinal axis and whereby the chamber is refilled from the bottle means by closing the valve means in the dispensing end and by opening the valve means in the piston means or tubular means and in the bottle; return means mounted on the assembly so as to move the piston means in the sleeve means back to the position for holding the liquid prior to dispensing and thus to refill the chamber; and additional one-way valve means for air inlet into the bottle means which allows air to enter the bottle means as the chamber in the sleeve means is refilled by movement of the piston means in the sleeve means back to the position for holding the liquid prior to dispensing;

(b) dispensing the liquid by pushing the syringe assembly against the animal; and (c) allowing the return means to move the piston means in the sleeve means to refill the chamber.

11. The method of claim 10 wherein the bottle means is mounted on the operator.

12. A syringe assembly for connection to a dispensing means which reloads a liquid to be dispensed by the syringe assembly after injecting a dose of the liquid into an animal which comprises:

(a) a piston means movable along a longitudinal axis for dispensing the liquid from the syringe assembly and which has an opening along the axis;

(b) a sleeve means confining the piston means for movement along the longitudinal axis and defining a chamber with the piston means for holding a liquid prior to dispensing, the sleeve means having a dispensing end with an opening for discharging the liquid and a charging end for receiving the liquid;

(c) tubular means connected at one end to the piston means along the longitudinal axis and extending from the charging end of the sleeve means to provide movement of the piston means in the sleeve means and to provide a fluid connection from the dispensing means to the opening in the piston means;

(d) handle means grippable by one hand mounted on the tubular means away from the charging end of the sleeve means such that the tubular means can be moved to push the piston means in the sleeve means along the longitudinal axis by the hand on the handle means;

(e) one-way valve means in the dispensing end of the sleeve means and the opening in the piston means or in the tubular means, whereby liquid can be dispensed from the chamber through the dispensing end of the sleeve means and needle means by the piston means with the valve means in the dispensing end open and with the valve means in the piston means or tubular means closed and whereby the chamber is refilled from the dispensing means by closing the valve means in the dispensing end and by opening the valve means in the piston means or tubular means; and (f) return means mounted on the assembly so as to move the piston means in the sleeve means back to the position for holding the liquid prior to dispensing and thus refill the chamber.

13. The syringe assembly of claim 12 wherein a coil spring means is provided as the return means around the tubular means between the sleeve means and the handle means to automatically retract the piston means in the sleeve means after the liquid is dispensed from the chamber.

14. The syringe assembly of claim 12 wherein each of the one-way valve means has a conical seat and a valve body which is conical and wherein each valve body is urged into a resting closed position by a valve coil spring which engages the valve body.

15. The syringe assembly of claim 12 wherein the tubular means slides in an adjustable threaded journal member mountd on threads in the sleeve means with a threaded nut on the journal member which abuts on the sleeve means to lock the journal member in position and wherein the journal member limits movement of the piston means in the sleeve means when chamber is refilled to thereby restrict the amount of fluid to be dispensed from the chamber.

16. The syringe assembly of claim 12 wherein the sleeve means comprises a cylindrical housing supporting the piston means and a cover over the housing with a threaded opening supporting a threaded journal member which engages the piston prior to dispensing the liquid mounting the tubular means and movable into and out of the housing to change the size of the chamber by limiting the movement of the piston means in the housing when the chamber is refilled in wherein a threaded nut is provided on the journal member which locks the threaded journal member in position by engaging the cap and wherein an adjusting knob is provided at an end of the journal member on an outside portion of the sleeve means and cover for adjusting the position of the journal member in the cover.

* * * * *